(12) United States Patent
Schostek et al.

(10) Patent No.: US 6,623,221 B2
(45) Date of Patent: Sep. 23, 2003

(54) ARTICULATED MILLING ARM FOR A DENTAL MILLING INSTRUMENT

(75) Inventors: Gerd Schostek, Gelnhausen (DE); Hartmut Brinkmann, Bohmte (DE); Klaus-Dietrich Lingemann, Osnabrück (DE); Otto Finke, Rehden (DE)

(73) Assignee: DeguDent GmbH, Hanau (DE)

( * ) Notice: Subject to any disclaimer, the term of this patent is extended or adjusted under 35 U.S.C. 154(b) by 98 days.

(21) Appl. No.: 09/827,320

(22) Filed: Apr. 6, 2001

(65) Prior Publication Data

US 2001/0044094 A1 Nov. 22, 2001

(30) Foreign Application Priority Data

Apr. 7, 2000 (DE) .......................................... 100 17 477

(51) Int. Cl.[7] ............................... B23D 7/00; B23C 1/00
(52) U.S. Cl. ...................... 409/235; 409/236; 409/230; 409/185; 409/190
(58) Field of Search .............................. 409/235, 236, 409/185, 190, 191, 204, 206, 210, 214, 229, 228, 230

(56) References Cited

U.S. PATENT DOCUMENTS

| | | | | |
|---|---|---|---|---|
| 3,938,865 A | * | 2/1976 | Rouverol ..................... | 384/550 |
| 4,118,141 A | | 10/1978 | Spohn, Jr. ..................... | 408/90 |
| 4,427,382 A | | 1/1984 | Hoffmeister et al. ........... | 433/79 |
| 4,608,825 A | * | 9/1986 | Fontaine ..................... | 180/272 |
| 5,110,241 A | * | 5/1992 | Shook ......................... | 409/235 |
| 5,344,264 A | * | 9/1994 | Hevoyan ..................... | 409/235 |
| 5,413,440 A | * | 5/1995 | Willson et al. ............. | 409/235 |
| 5,697,475 A | * | 12/1997 | Le Deit et al. ......... | 188/205 R |
| 5,788,023 A | * | 8/1998 | Schoner et al. ............. | 188/158 |
| 6,119,580 A | * | 9/2000 | Sato et al. ................. | 29/527.5 |

FOREIGN PATENT DOCUMENTS

| | | |
|---|---|---|
| DE | 31 15 230 | 11/1982 |
| DE | 39 30 154 | 3/1991 |
| FR | 2 545 744 | 11/1984 |

\* cited by examiner

*Primary Examiner*—A. L. Wellington
*Assistant Examiner*—Dana Ross
(74) *Attorney, Agent, or Firm*—Smith, Gambrell & Russell, LLP

(57) ABSTRACT

An articulated milling arm for a milling instrument, which includes a milling arm support movably attached to a frame to allow vertical displacement of the milling arm support; a first vertical axle, rotatably connecting the first milling arm support to a middle portion of the milling arm to allow swiveling of the middle portion of the milling arm horizontally about a vertical axis of the first vertical axle, the first vertical axle being provided with a braking surface; a second vertical axle, rotatably connecting the middle portion of the milling arm to a milling unit support to allow swiveling of the milling unit support horizontally about a vertical axis of the second vertical axle, the second vertical axle also being provided with a braking surface. The milling arm is provided with a movable braking plate, on the middle portion of the milling arm, which movably contacts the braking surface of the first vertical axle and the breaking surface of the second vertical axle. The invention further provides that the common braking plate is pressurized pneumatically or hydraulically via a diaphragm which presses against the braking surfaces of the two vertical axles in order to fix the articulated milling arm horizontally.

10 Claims, 2 Drawing Sheets

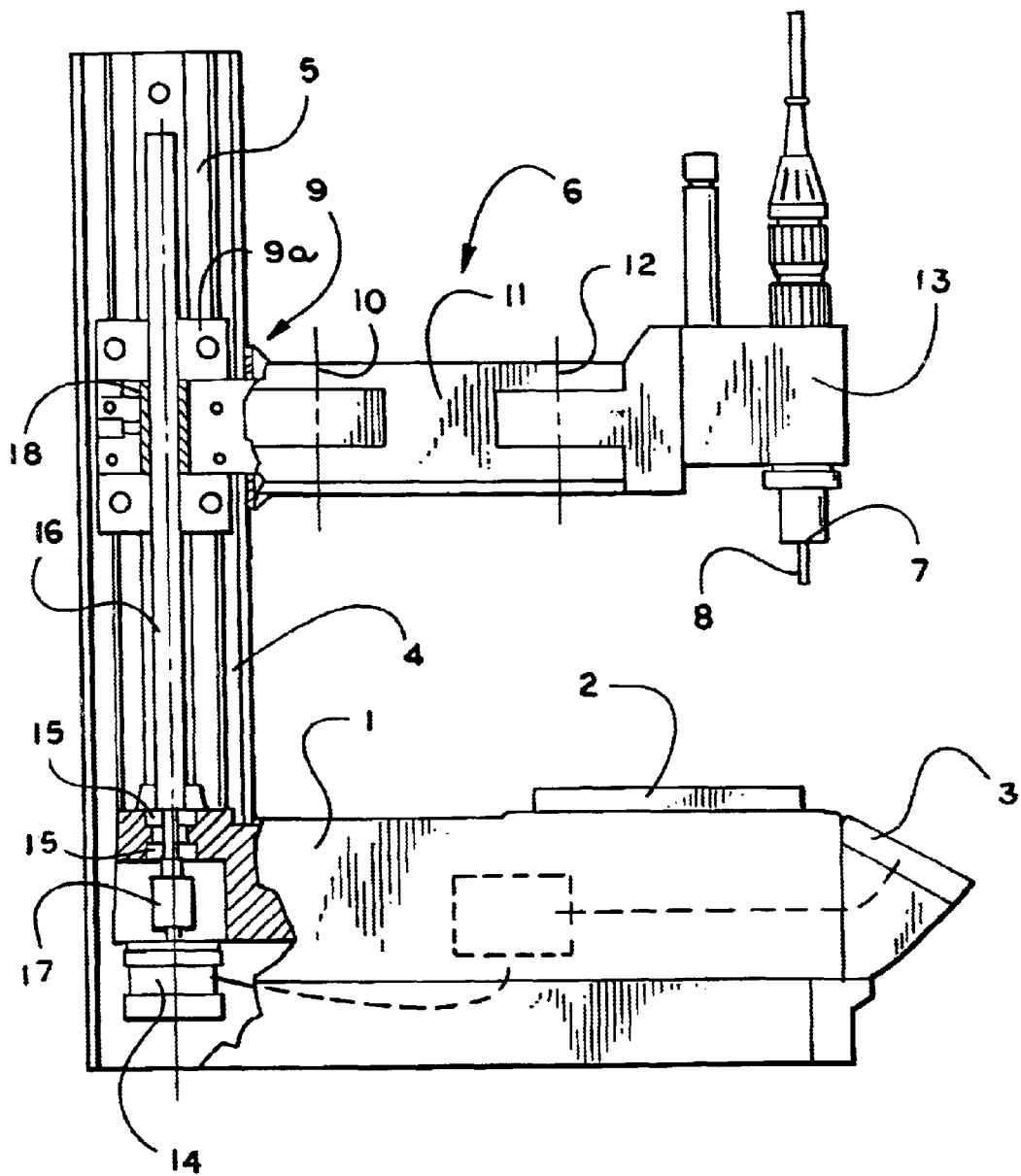
Fig_1

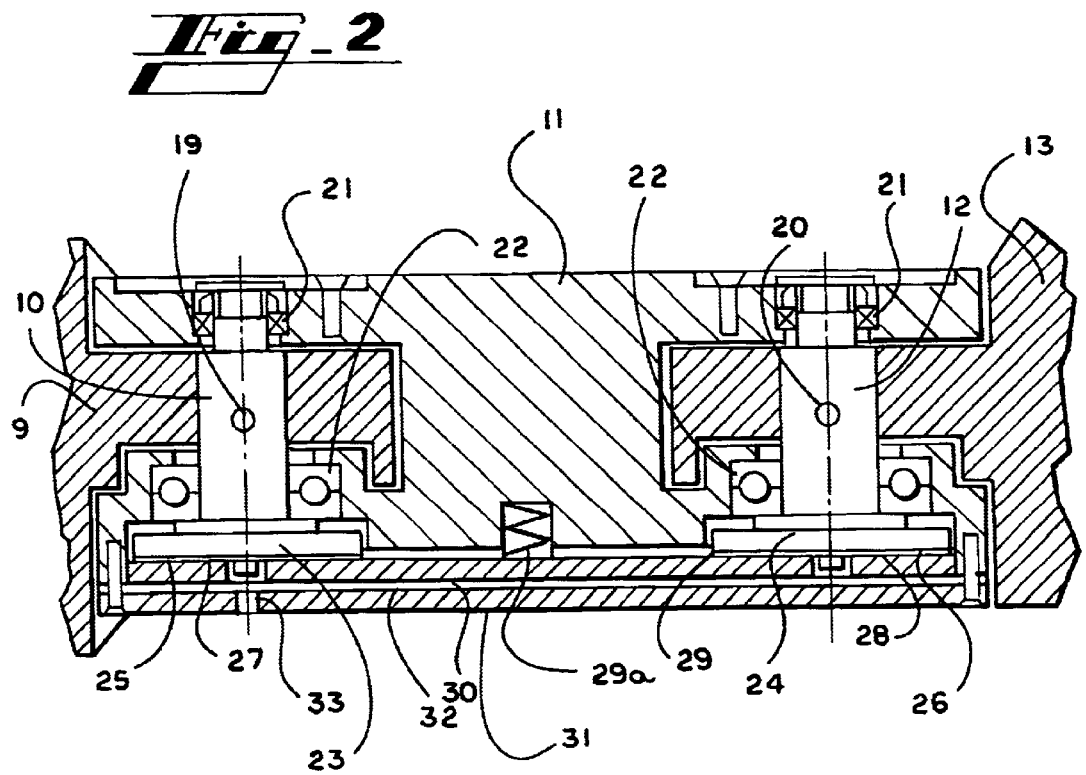
*Fig_2*
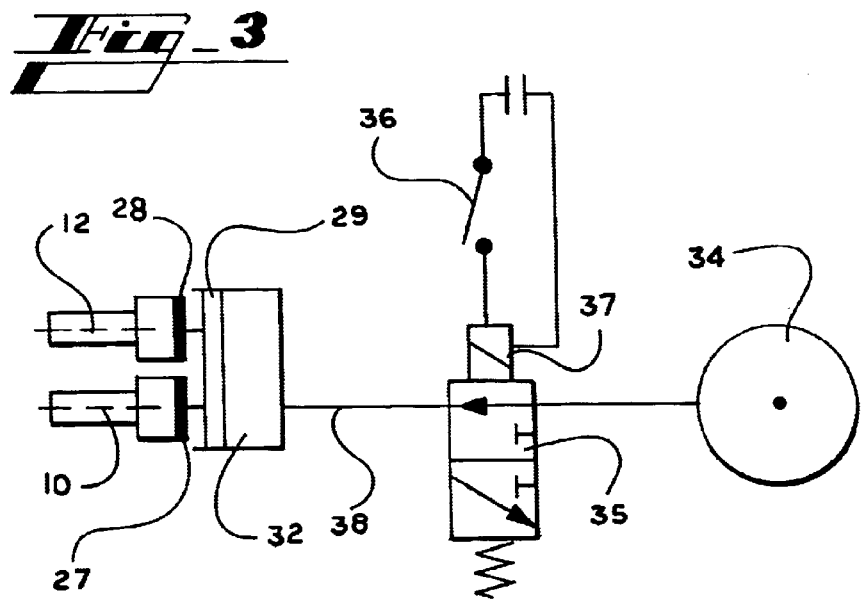
*Fig_3*

ARTICULATED MILLING ARM FOR A DENTAL MILLING INSTRUMENT

BACKGROUND OF THE INVENTION

1. Field of the Invention

The invention relates to an articulated milling arm for a dental milling instrument, the middle portion of the milling arm being connected in a horizontally swivelling manner to a first vertical articular axle which is fixed with respect to the frame, and to a second vertical articular axle which is rigidly connected to a support for a milling unit, with a common clamping device acting on both articular axles for the purpose of fixing the articulated milling arm.

2. Description of the Related Art

When dental objects such as dental casts and prosthodontic parts are milled, certain milling processes can only be carried out with a milling unit that is mobile in the horizontal plane, due to the anatomical tooth shapes which are to be milled. A horizontally mobile articulated milling arm is therefore required for this purpose, the support for which conventionally comprises a linear unit which enables a movement of the milling unit perpendicular to the plane of movement of the articulated milling arm. Known articulated milling arms for such dental milling instruments typically consist of several articulated arm members connected by articulations, which enable the requisite mobility in the horizontal plane.

For other processing operations typically carried out with such dental milling instruments, for example drilling or thread cutting, it is necessary to construct the articulated milling arm to be rigid and, particularly in the horizontal plane, immovable, whereby only the linear unit which is fitted to the articulated milling arm is permitted to exhibit a degree of freedom in the direction of the processing axis. Because such drilling and cutting operations have to be performed with a high degree of precision, the articulated milling arm which is rigid during processing has to exhibit a high degree of stiffness and inflexibility.

In order to satisfy these contradictory requirements, dental milling instruments have been developed which comprise two different milling arms: one milling arm being of articulated construction and exhibiting the required horizontal mobility, whereas a second milling arm is of rigid construction and exhibits the requisite stiffness and inflexibility for the intended drilling and cutting operations. The efforts required for such constructions are considerable.

Other known milling instruments resolve these requirements by providing articulations of the articulated milling arm which are capable of being fixed by clamping devices. As a result, a second, rigid milling arm can be dispensed with. In the case of a known dental milling instrument (DE 36 11 518 C2), a mechanical fixation of the articulations is accomplished by means of mechanical clamping devices which have to be actuated separately, for example by means of toggles or handwheels. In this case, the construction of several grips is required in order to fix the articulated milling arm. In addition, the locking action depends on the manual forces applied in each instance by the user.

It is also known to provide a separate electromagnetic braking device for each articulation of an articulated milling arm for a dental milling instrument. Although it is possible to remotely control the device by this means, the efforts in constructing such a device are considerable. Also, due to the type of construction, the clamping forces which can be achieved are relatively small, so that in the case of greater loads, a yielding of the lock results in imprecise operations. This disadvantage also exists in the case of a mechanical lock, if the clamping forces to be applied by the user are undefined or are too small, so that in this instance also there is a risk of imprecise operations.

In the case of a known articulated milling arm of the type specified at the outset (DEG 94 16 767.2 U1), the common clamping device acting on the two articular axes is actuated by means of a wing nut that has to be tightened by hand. Also in this case, the clamping forces achieved depend on the manual force applied in each instance by the user; the sequence of movements for which is not ergonomic. Further, this configuration does not allow remote control.

It is therefore an object of the invention to design an articulated milling arm in such a way that with a relatively simple structural configuration, high clamping forces can be applied to the articulations of the articulated milling arm by remote control, so that a reliable and ergonomically advantageous sequence of operations is made possible.

SUMMARY OF THE INVENTION

The invention provides an articulated milling arm designed in such a way that with a relatively simple structural configuration, high clamping forces can be applied to the articulations of the articulated milling arm by remote control, so that a reliable and ergonomically advantageous sequence of operations is possible. The invention provides two articular axles, each comprising a braking surface, and an axially mobile braking plate capable of being pressed against both braking surfaces by means of a common brake-actuating device which is actuated by pressure means.

The actuation of the common braking plate by pressure means enables the application of high braking forces to both articulations, so that a reliable fixation of the articulated milling arm is ensured. The remote control of the brake-actuating device enables a simple and ergonomic sequence of operations, whereby the high clamping forces that are applied do not depend on the manual force of the user.

The braking plate is preferably connected to a pneumatically or hydraulically pressurizable diaphragm having a large area. The use of a diaphragm as a driving member which is actuated by pressure means enables a relatively simple type of construction with large surfaces which are pressurized by pressure means, so that high clamping forces can be generated with relatively low pressure.

The diaphragm preferably bears against the braking plate. A pressure chamber, located on the opposite side of the diaphragm, is preferably capable of being pressurized pneumatically or hydraulically. This results in a particularly simple transmission of the pneumatically- or hydraulically-generated forces to the braking plate.

It is particularly advantageous if the pressure chamber extends substantially over the entire area of the braking plate. By this arrangement, the entire available area of the braking plate is pressurized.

Further advantageous configurations of the inventive concept are described in the claims of the application. Additional variations and modifications will be apparent to those skilled in the art.

BRIEF DESCRIPTION OF THE DRAWINGS

The invention will be better understood with reference to the accompanying drawings, in which:

FIG. 1 depicts a dental milling instrument according to the invention in a side view, which is partially in section;

FIG. 2 depicts an enlarged vertical partial sectional view through the articulated milling arm of the milling instrument according to FIG. 1; and FIG. 3 depicts a circuit diagram of a brake-actuating device, which is capable of being actuated by pressure means, for the articulated milling arm according to FIG. 2.

DETAILED DESCRIPTION OF THE INVENTION

A base 1 of the dental milling instrument according to FIG. 1 supports a working table 2 and an electrical operating panel 3. The working table 2 serves to receive the dental objects to be processed. The base 1 is connected to a vertical guide column 4 which comprises a guideway 5 for an articulated milling arm 6 which supports a milling unit 7 in which an interchangeable milling or drilling tool 8 is received. The articulated milling arm 6 comprises a milling-arm support 9 which is capable of being displaced along the guideway 5 of the guide column 4 and which forms a supporting slide 9a. The supporting slide 9a is connected in a horizontally swivelling manner to a middle portion 11 of the milling arm via a first vertical swivel axle 10. The middle portion 11 of the milling arm is connected in swivelling manner to a support 13 for the milling unit 7 via a second vertical swivel axle 12.

The vertical movement and vertical positioning of the articulated milling arm 6 are effected by means of an electromotive height-adjusting drive which comprises a screw link actuator that is capable of being driven by an electrical adjusting motor 14. A threaded spindle 16 which is supported in the base 1 in bearings 15, and which extends along the vertical guide column 4, is connected to the adjusting motor 14 via a coupling 17. The threaded spindle 16 is in engagement with a spindle nut 18 which is arranged in the supporting slide 9a.

As represented in detail in FIG. 2, the first articular axle 10 is rigidly connected to the milling-arm support 9 via a pin 19. Similarly, the second articular axle 12 is rigidly connected to the support 13 via a pin 20. The middle portion 11 of the milling arm is supported via roller bearings 21, 22 on the two swivel axles 10, 12 so as to be capable of swivelling about the vertical axles. Preferably, at least the bearings 22 are constructed as thrust bearings, preferably as tapered roller bearings.

Fitted frontally on each of the two articular axles 10, 12 is a braking disc 23 and 24, respectively. The two braking discs each bear a friction lining 25 and 26, respectively, which each form a frontal braking surface 27 and 28, respectively.

On the underside of the middle portion 11 of the milling arm a braking plate 29 that is capable of being pressed against the two braking surfaces 27, 28 is received in an axially mobile manner.

A flexible diaphragm 30 bears against the side of the braking plate 29 located opposite the braking surfaces 27, 28. Between a cover plate 31 extending over the entire outer surface of the diaphragm 30, and the diaphragm 30, a pressure chamber 32 is formed which extends substantially over the entire area of the braking plate 29, and which, via a bore 33, is capable of being pressurized pneumatically or hydraulically by pressure means. The diaphragm 30 is tightly clamped at its edge between the middle portion 11 of the milling arm and the cover plate 31. The volume of the pressure chamber 32 is very small, so that only a very small amount of air is required for the actuation of the clamping device.

Between the middle portion 11 of the milling arm and the braking plate 29 there is arranged a spring 29a, which in this example is constructed as a compression spring, and which the braking plate 29 away from the braking surfaces 27, 28 in the unpressurized state. By this means, ease of movement is ensured in the course of free milling with a mobile articulated milling arm.

FIG. 3 shows the pneumatic brake-actuating device in a schematic circuit diagram. A compressed air reservoir 34 is connected to a switch valve 35 which, in the embodiment example represented, is actuated via an actuating switch 36 and a relay 37. Instead of this arrangement, a manual actuation of the switch valve 35 is also possible. The switch valve 35 supplies the requisite actuating pressure to the pressure chamber 32 via a line 38. The braking plate 29 is pressed against the two braking surfaces 27 and 28, and brings about a nonpositive, rigid connection of the braking plate 29 to the two articulated axes 10 and 12. Instead of the pneumatic actuation that has already been described, a hydraulic actuation is also possible. Generation of the necessary pressure can also be effected via an external pump or a pump that is integrated within the instrument.

In addition to the axial pressurization of the braking surfaces on the two articular axles 10 and 12, which has been described, embodiments are also possible in which pressure is exerted radially on the braking surfaces on the articular axes 10 and 12.

Further variations and modifications will be apparent to those skilled in the art from the foregoing, and are intended to be encompassed by the invention according to the claims which follow.

German priority application 100 17 477.9 is relied on and incorporated herein by reference.

We claim:

1. An articulated milling arm for a milling instrument, comprising:

a milling arm support, movably attached to a frame which allows vertical displacement of the milling arm support;

a first vertical axle, rotatably connecting the first milling arm support to a middle portion of the milling arm to allow swiveling of the middle portion of the milling arm horizontally about a vertical axis of the first vertical axle, the first vertical axle being provided with a braking surface;

a second vertical axle, rotatably connecting the middle portion of the milling arm to a milling unit support to allow swiveling of the milling unit support horizontally about a vertical axis of the second vertical axle, the second vertical axle being provided with a braking surface; and a movable braking plate, provided on the middle portion of the milling arm, which movably contacts the braking surface of the first vertical axle and the braking surface of the second vertical axle by a common brake-activating device which includes a pneumatically or hydraulically pressurizable diaphragm, wherein a pressure chamber is provided on a side of the diaphragm opposite the movable braking plate, which pressure chamber is pressurized pneumatically or hydraulically, thereby causing the diaphragm, to bear against the braking plate.

2. The articulated milling arm according to claim 1, wherein the pressure chamber extends over substantially an entire area of the braking plate.

3. An articulated milling arm for a milling instrument, comprising:

a milling arm support, movably attached to a frame which allows vertical displacement of the milling arm support;

a first vertical axle, rotatably connecting the first milling arm support to a middle portion of the milling arm to allow swiveling of the middle portion of the milling arm horizontally about a vertical axis of the first vertical axle, the first vertical axle being provided with a braking surface; a second vertical axle, rotatably connecting the middle portion of the milling arm to a milling unit support to allow swiveling of the milling unit support horizontally about a vertical axis of the second vertical axle, the second vertical axle being provided with a braking surface;

a movable braking plate, provided on the middle portion of the milling arm, which movably contacts the braking surface of the first vertical axle and the braking surface of the second vertical axle; and a spring provided in operable contact with the braking plate, which causes the braking plate to be lifted away from the braking surfaces when the braking plate is not in contact with the braking surfaces.

4. An articulated milling arm for a milling instrument, comprising:

a milling arm support, movably attached to a frame which allows vertical displacement of the milling arm support;

a first vertical axle, rotatably connecting the first milling arm support to a middle portion of the milling arm to allow swiveling of the middle portion of the milling arm horizontally about a vertical axis of the first vertical axle, the first vertical axle being provided with a braking surface;

a second vertical axle, rotatably connecting the middle portion of the milling arm to a milling unit support to allow swiveling of the milling unit support horizontally about a vertical axis of the second vertical axle, the second vertical axle being provided with a braking surface;

a movable braking plate, provided on the middle portion of the milling arm, which movably contacts the braking surface of the first vertical axle and the braking surface of the second vertical axle; wherein the braking surface of the first vertical axle and the braking surface of the second vertical axle are braking discs fitted to the vertical axles.

5. The articulated milling arm according to claim 4, wherein each of the braking discs is provided with a friction lining.

6. An articulated milling arm for a milling instrument, comprising:

a milling arm support, movably attached to a frame which allows vertical displacement of the milling arm support;

a first vertical axle, rotatably connecting the first milling arm support to a middle portion of the milling arm to allow swiveling of the middle portion of the milling arm horizontally about a vertical axis of the first vertical axle, the first vertical axle being provided with a braking surface;

a second vertical axle, rotatably connecting the middle portion of the milling arm to a milling unit support to allow swiveling of the milling unit support horizontally about a vertical axis of the second vertical axle, the second vertical axle being provided with a braking surface;

a movable braking plate, provided on the middle portion of the milling arm, which movably contacts the braking surface of the first vertical axle and the braking surface of the second vertical axle; and wherein the movable braking plate contacts the braking surfaces by means of a common brake-actuating device wherein the common brake-actuating device further comprises a pressure chamber which is provided on a side of the diaphragm opposite the movable braking, which pressure chamber is pressurized pneumatically or hydraulically, and which causes the diaphragm to bear against the braking plate.

7. The articulated milling arm according to claim 6 wherein the pressure chamber extends over substantially an entire area of the braking plate.

8. The articulated milling arm according to claim 6 wherein a spring is provided in operable contact with the braking plate, which causes the braking plate to be lifted away from the braking surfaces when the braking plate is not in contact with the braking surfaces.

9. The articulated milling arm according to claim 6 wherein the braking surfaces comprise braking discs which are fitted to the vertical axles.

10. The articulated milling arm according to claim 9, wherein each of the braking discs is provided with a friction lining.

* * * * *